United States Patent [19]

Kifune et al.

[11] Patent Number: 4,651,725

[45] Date of Patent: Mar. 24, 1987

[54] WOUND DRESSING

[75] Inventors: Koji Kifune, Nara; Yasuhiko Yamaguchi; Hiroyuki Tanae, both of Kyoto, all of Japan

[73] Assignee: Unitika Ltd., Hyogo, Japan

[21] Appl. No.: 852,246

[22] Filed: Apr. 15, 1986

[30] Foreign Application Priority Data

Apr. 18, 1985 [JP] Japan .................................. 60-85169

[51] Int. Cl.$^4$ ............................................. A61L 15/00
[52] U.S. Cl. .................................................. 128/156
[58] Field of Search ................... 128/156, 334 R, 335; 428/310, 316–317, 332, 478.2; 424/28, 177; 106/141, 155

[56] References Cited

U.S. PATENT DOCUMENTS

| | | | |
|---|---|---|---|
| 4,233,360 | 11/1980 | Luck | 128/156 |
| 4,236,550 | 12/1980 | Braun | 128/156 |
| 4,292,299 | 9/1981 | Suzuki | 128/156 |
| 4,292,972 | 10/1981 | Pawelchak | 128/156 |
| 4,296,745 | 10/1981 | Raymond | 128/156 |

*Primary Examiner*—Gregory E. McNeill
*Attorney, Agent, or Firm*—Wenderoth, Lind & Ponack

[57] ABSTRACT

Disclosed is a wound dressing comprising a nonwoven fabric composed of
  (A) a chitin fiber having a thickness of less than one denier and a strength of not less than 2 g/d, and
  (b) a fibrous binder, which is suitable for dressings of skin defect wounds, which has compatibility to a living body and good fitness property to the surface of wounds and which is insoluble with exudates.

4 Claims, No Drawings

WOUND DRESSING

FIELD OF THE INVENTION

The present invention relates to a wound dressing composed of a nonwoven fabric of chitin fibers. More particularly, it relates to a wound dressing suitable for the protection of skin defect wounds, which has compatibility to a living body and good fitnessn property to the surface of wounds and which is insoluble with exudates.

BACKGROUND OF THE INVENTION

Many materials have been proposed as skin defect wound dressings of burns, donor sites, skin graft site and e.t.c. These dressings are generally classified to those made from synthetic materials and those made from natural materials. Examples of synthetic materials are velour fabric made from nylon fibers or polyester fibers, polyurethane foam sheet, cross-linked polyvinylalcohol foam sheet and the like. Examples of natural materials are collagen nonwoven fabric (commercially available from Meiji-Seika Kaisha Ltd as Meipack), freeze-dried pig-skin (commercially available from Mitsui Pharmaceutical Co. Ltd. as Methaskin) and fibrin membrane. Biological dressings derived from natural materials become more polular as the dressings of skin defect wounds because of high compatibility to a living body.

However, these biological dressings such as collagen nonwoven fabrics or freeze-dried pig-skins have some defects. One of defects is inferior fitnessn to the surface of wounds. Such dressings are required to have an function as an artificial skin to some degree, because it is preferred that the dressings work together with the surface of wounds to heal. In case where the adhesion of the protectors to the surface of wounds is insufficient, much exudates stay between the protector and the surface of wounds and delays drying so as to cause preventing epidermidation. The second defect is that the dressing may be easily decomposed in an early stage. These decompositions not only loss the function of the dressing but also cause infections. As the result the epidermidation is badly affected. The third defect is that it is difficult to absorb the exudate being produced in the surface of the skin. This provides the same result as the first defect. Accordingly, a dressing without having the above defects is desired among the natural materials.

On the other hand, it has been proposed that chitin can be adopted as the wound dressing in the form of nonwoven fabrics composed of chitin fiber, because chitin, which is an aminopolysuccharide containing in exoskeletons of Crustacea, Insecta and the like, has excellent compatibility to a living body when purified. For example, in Proceedings of the 1st Int. Conference on chitin/chitosan (1977), page 300 (hereinafter referred to as "Conference"), chitin nonwoven fabrics are disclosed, wherein the chitin nonwoven fabrics are made by dispersing chitin fibers having a length of 30 mm in water and then removing water. Japanese Patent Publication (unexamined) Nos. 26049/1981 and 16999/1982 also disclose nonwoven fabrics using chitin fibers. Further, U.S. Pat. No. 4,431,601 (corresponding to Japanese Patent Publication (unexamined) No. 77310/1982) discloses chitin fibers having a thickness of 0.5 to 20 denier and a strength of 2 g/d.

These chitin fabrics, however, are not always sufficient as the wound dressings in comparison with the conventional biological dressings. Fiber size is for example 0.15 mm in Conference, 1 to 5 denier in Japanese Patent Publication (unexamined) No. 26049/1981, less than 10 denier (typically 3 denier) in Japanese Patent Publication (unexamined) No. 16999/1982. Japanese Patent Publication (unexamined) No. 16999/1982 does not teach use of binder and Japanese Patent Publication 26049/1981 employs a chitin dope as a binder. Japanese Patent Publication (unexamined) No. 16999/1982 discloses the fiber strength of 1 g/d, but it is not sufficient for wound dressing. Nonwoven fabrics disclosed in the above references have inferior fitness and easy decomposition with exudates, and they are insufficient in the exclusion of the exudate to outside when they are used for the wound dressing.

SUMMARY OF THE INVENTION

The present invention is to provide a nonwoven fabric of chitin suitable for a wound dressing. The wound dressing of the present invention is formed from a nonwoven fabric composed of (A) a chitin fiber having a thickness of less than one denier and a strength of not less than 2 g/d, and (B) a fibrous binder.

DETAILED DESCRIPTION OF THE PRESENT INVENTION

In the present invention, chitin includes both chitin per se and a derivative thereof. By "chitin" is meant poly(n-acetyl-D-glucosamine) prepared by treating exoskeletons of Crustacea or Insecta with hydrochloric acid and caustic soda to remove calcium and protein. The derivatives include those patially deacetylized (so-called chitosan), etherified, esterified, carboxymethylated, hydroxyethylated or o-ethylated. Representative examples of the derivatives are poly-(N-acetyl-6-o-(2'-hydroxyethyl)-D-glucosamine), poly-(N-acetyl-6-o-ethyl-D-glucosamine) and the like.

The chitin fiber constituting the nonwoven fabric in the present invention has a thickness of less than one denier and a strength of not less than 2 g/d. The chitin fiber can be prepared by methods described in U.S. Pat. No. 4,431,601. For example, chitin is dissolved in a suitable solvent to obtain a dope. In this context, the solvent may be an N-methylpyrrolidone solution containing lithium chloride, a dimethylacetoamide solution containing lithium chloride, a mixture solution of trichroloacetic acid and a halogenated hydrocarbon, when the chitin to be used contains acetylglucosamine group in large quantities. When the chitin contains glucosamine group in large quantities (referred to as chitosan in general), it is preferred that the solvent may be an acid solution such as acetic acid. The dope preferably contains chitin in a concentration of 0.5 to 20% by weight. The dope is filtered with a stainless net and the like to remove undissolved materials and dusts and extruded into a coagulation solution through a nozzle having 20 to 5,000 holes and a hole diameter of 0.03 to 0.2 mm preferably in a constant amount controlled by a gear pump and the like. Examples of the coagulation solution are water, alcohols such as methanol, ethanol, propanol, butanol and the like, and ketones such as acetone. The coagulated filament is taken out in a rate of 2 to 50 m/min by a spining roller and then wound with a winder and so on under substantially no tension or a reduced tension. The filaments are recoagulated in the same coagulation solution and rinsed to remove a solvent associated with the filaments followed by drying. In the practice of the present invention, the preferred chitin fiber has a thickness of not less than 0.2 denier and less than 1 denier. The denier is determined by measuring the weight of a sample of 90 m of the chitin fiber at 65% RH and 25° C. and changing it into 9,000 m. Such thin chitin fiber, when applied to a wound dressing in the form of nonwoven fabrics, enhances fitness to the surface of the wounds and no peelings occur after several days, whereby the epidermidation will be attained in early stage to provide good healing conditions. It is believed that this effect is related to the fact that the thin chitin fibers have high permeation rate of water in comparison with conventional thick chitin fibers. The chitin fiber of the present invention has a strength of not less than 2 g/d, preferably not less than 3 g/d. The strength is determined by a tension tester "TENSILON UTM-II TYPE" (available from Toyo Boldwin Co. Ltd.) in the conditions of a filament length of 50 mm, the tension speed of 20 mm/min, 25° C. and 65% RH. Strengths less than 2 g/d are not desirable because the wound dressing is easily decomposed by body fluids from the wounds, such as exudate to disappear its shape. Preferred length of the chitin fiber of the present invention is within the range of 3 to 20 mm.

The fibrous binder constituting the nonwoven fabric of the present invention is obtained from a resin binder which is usually used as adhesives in a conventional production of nonwoven fabric. The resin binder is shaped to a fiber having a thickness of 0.1 to 50 d and a length of 0.5 to 150 mm, preferable a thickness of 0.5 to 10 d and a length of 1 to 20 mm. Examples of the resin binders are polyvinyl alcohol, carboxymethyl cellulose, gelatin, starch, acrylic acid ester, vinyl acetate, ethylene, vinyl acetate copolymer, vinyl chloride, natural rubber, a synthetic rubber. Preferred fibrous binder is polyvinyl alcohol fiber preferably having a degree of polymerization of 500 to 3,000, a degree of hydrolysis of not less than 95 mole %, more preferably not less than 99%.

Production of the nonwoven fabric can be carried out by a similar process to paper making. Conventional continuous paper machines or batch type paper machine may by employed. The weight ratio of the chitin fiber to the fibrous binder is preferably within the range of 80:20 to 95:5.

In the production of the nonwoven fabric by a batch process, the above fiber and fibrous binder are dispersed in water at an ambient temperature in a constant weight ratio mentioned above and passed a filter having 20 to 200 mesh through the dispersion in the batch to form a layer of the dispersed fibers on the filter. After pressing to squeeze water, the fiber layer is dried by pressing between a thick cloth and a rotary heat roller for 3 to 20 minutes at 100° to 180° C. in a roller type heat-press drier. The amount of the fiber and fibrous binder is varied depending on thickness and weight of desired nonwoven fabrics. Since it is preferred that the thickness of the nonwoven fabrics is 0.05 to 0.5 mm and the weight is 1 to 10 mg/cm$^2$, the dispersed amount can be selected.

The obtained nonwoven fabrics are flexible and very strong, and would be a good protector for covering wounds when they are sterilized.

The present invention will be illustrated by the following examples, but they are not construed as limiting the scope of the present invention.

EXAMPLE 1 AND COMPARATIVE EXAMPLE 1 AND 2

A chitin powder (available from Kyowa Yushi Co. Ltd.) was ground to 100 mesh and treated in 1N-HCl for one hour at 4° C. It was then heated to 90° C., at which it was treated for 3 hours in a 3% NaOH solution to remove calcium and protein in the chitin powder, and rinsed repeatedly followed by drying it. The resultant chitin had 256 centipoise at 30° C. when it was dissolved in a dimethylacetoamide solution containing lithium chloride of 8 wt % to form a 0.2 wt % solution. This chitin was dissolved in a dimethylacetoamide solution containing lithium chloride of 7 wt % to form a 7% dope. After filtering and holding for defoaming, the dope was sent to a nozzle having a diameter of 0.06 mm and 200 holes from a charged tank under pressure by a gear pump to extrude into butanol at 60° C. at the rate of 2.2 g/min. The chitin was cogulated and taken out at the speed of 10 m/min. The resultant strand was rinsed with water and dried to obtain a filament having 0.68 denier in single yarn denier and 3.1 g/d in strength.

For a comparison, pump out put was set to 3.8 g/min and 7.4 g/min and treated as mentioned above to obtain a filament for Comparative Example 1 having a single-yarn denier of 1.2 d and a strength of 3.0 g/d and a filament for Comparative Example 2 having a single-yarn denier of 2.3 d and a strength of 3.1 g/d.

The obtained filaments were cut to 8 mm, from which nonwoven fabrics were formed as follow. The preparation apparatus was a Sheet Machine TAPPI-T205os-71 available from Toyo Seiki Product. 0.5 g of the chitin fiber and 0.05 g of a polyvinyl alcohol fiber having 1 mm length, a degree of polymerization of 1,700 and a degree of hydrolysis of 99.7% (available from Unitika Kasei Co. Ltd. as Unitika Newlon SML) were dispersed in one liter of water. Water was further added to the resultant dispersion to make a uniform dispersion of 6 liter and charged in the sheet machine. A stainless net was passed through the dispersion to form a fibrous layer on it. The fibrous layer was held between two piece of qualitative filer paper and pressed under the pressure of 3 Kg/mm$^2$ by a pressing machine to remove water. The layer was further dried for 6 minutes over a rotaly heat roller having 150° C. by pressing it between a thick cloth and the rotary heat roller to form three piece of nonwoven fabric. The thickness of these fabrics were shown in Table 1 and the weight of them was 3 mg/cm$^2$. The three nonwoven fabrics were tested in stiffness. The result is shown in Table 1.

TABLE 1

|  | Thickness of sheet (mm) | Stiffness[1] (g/cm$^2$) |
| --- | --- | --- |
| Example 1 | 0.16 | 375 |
| Comparative Ex. 1 | 0.15 | 832 |
| Comparative Ex. 2 | 0.16 | 933 |

[1]A sample having 0.5 cm width and 2 cm length was placed on the diameter of the upper surface of a cylinder having 1 cm inside diameter, 1.4 cm outside diameter and 0.3 cm height, what is fixed outside and placed horizontally. The center of the sample was caught by a hook which was connected to a strain gauge for 100 mg through the inside of the cylinder. The strain gauge was pulled downward at a speed of 5 cm/min to slip down the sample. The maximum value of the load was read and it was divided by the sectional area of the sample to indicate as stiffness.

As shown by Table 1, the nonwoven fabric of Example 1 has least stiffness, showing it is soft.

In order to evaluate the nonwoven fabric as a wound dressing, the skin of a rabbit was removed from a back portion, to which the fabrics were attached. The nonwoven fabric of Example 1 was fitted to the portion, while the nonwoven fabrics of Comparative Example 1 and 2 were stiff and did not fit into the surface of muscle.

EXAMPLE 2

A chitosan (available from Kyowa Yushi Co. Ltd.), which has 32 centipoise at 20° C. when it is dissolved in a a 0.2M acetic acid solution to form a 0.2 wt % solution, was dissolved in 0.2M acetic acid solution to form a 6 wt % solution. The solution was filter with a 1,480 mesh stainless net to obtain a viscous solution. The viscous solution was sent to a nozzle having 0.6 mm in diameter and 100 holes by a gear pump and extruded into a 1N caustic soda solution at the rate of 1.9 g/min to coagulate. The coagulated strand was further coagulated for about one hour in a 1N caustic soda solution and neutralized with a dilute chloric acid followed by rinsing and drying. The resultant filament had 0.53 d in a single yarn denier and 3.5 g/d in strength. The filament was cut to 10 mm and treated as generally described in Example 1 to form a nonwoven fabric with the exception that 0.3 g of the chitosan fiber and 0.05 g of polyvinyl alcohol fiber (Unitika Newlon SML) were dispersed in one liter of water, to which four liter of water was added.

The obtained nonwoven fabric has a thickness of 0.13 mm and a stiffness of 320 g/cm$^2$ and is very flexible. The fabric fitted into a muscle surface of a rabbit when it was attached to a skin removed portion of the rabbit back. This shows that the fabric is suitable as a wound dressing.

EXAMPLE 3 TO 6 AND COMPARATIVE EXAMPLE 3 TO 6

By adopting the same spining method as Example 1 using the dope of Example 1 with exception that the nozzle had 0.06 mm diameter and 200 holes, 8 kinds of filaments having different single yarn denier, 0.37 d (3.5 g/d strength), 0.47 d (3/5 g/d), 0.66 d (3.3 g/d), 0.80 d (3.4 g/d), 1.32 d (3.3 g/d), 1.81 d (3.2 g/d), 2.39 d (3.1 g/d) and 3.38 d (3.0 g/d), were obtained. These filaments were cut to 8 mm and nonwoven fabrics were formed as generally described in Example 1. The basis weight of each nonwoven fabric was 3 mg/cm$^2$.

The eight kinds of nonwoven fabrics were cut to 5 mm in width and 10 cm in length to form 8 ribbon shape samples. The samples were immersed in a physiological saline of 25° C. and measured the period when the saline rised up to 20 mm height from the liquid surface. The measurment was conducted ten times for each ribbon and the average was calculated as a rising rate. The result is shown in Table 2.

TABLE 2

| | Denier (d) | Thickness (mm) | Rising rate (mm/min) |
|---|---|---|---|
| Example 3 | 0.37 | 0.148 | 65.2 |
| Example 4 | 0.47 | 0.149 | 50.1 |
| Example 5 | 0.66 | 0.148 | 35.3 |
| Example 6 | 0.80 | 0.151 | 23.8 |
| Comparative Example 3 | 1.32 | 0.152 | 14.5 |
| Comparative Example 4 | 1.81 | 0.147 | 12.2 |
| Comparative Example 5 | 2.39 | 0.150 | 12.9 |
| Comparative Example 6 | 3.38 | 0.153 | 9.8 |

As shown in Table 2, the rising rate is very high in Examples, compared with Comparative Examples. It is shown that the nonwoven fabric of Examples is permeable by a physiological saline.

The nonwoven fabrics of Example 5 and Comparative Example 4 were cut to 10 cm in width and 10 cm in length and sterilized by ethylene oxide gas. The fabrics were subjected to a halfside test in which half of a donor site (0.021 inch depth, 3 cm width and 5 cm length) was covered by the nonwoven fabrics of Example 5, and the remaining half was covered by the other one. The dressings were fixed outside with a cotton gauze. After three days, the fabric of Example 5 was attached to the wound portion in good condition and the surface having been covered was kept in a proper wet condition, while the fabric of Comparative Example 4 was partially rised up from the wound portion and exudates were observed in many portions. After another 10 days, the wound portion covered by the fabric of Example 5 was completely healed to form a smooth surface, while the portion covered by the fabric of Comparative Example 4 was not completely healed and many red spots were observed.

EXAMPLE 7 AND COMPARATIVE EXAMPLE 7

A chitin fiber having 0.81 d in single yarn denier was obtained by extruding at 2.6 g/min in the same method as Example 1. The strength of the fiber was 3.4 g/d. The fiber was cut to 5 mm and a nonwoven fabric was formed as generally described in Example 1.

For a comparison, a nonwoven fabric was formed as generally described in Japanese Patent Publication (unexamined) No. 16999/1982. The preparation method is shown as follow: 7.7 parts by weight of the chitin of Example 1 and 91.4 parts by weight of formic acid were repeated to freeze and resolve to form a gelation, to which 7.7 parts by weight of dichloroacetic acid was added to form a dope. The dope was extruded from a platinum nozzle (0.1 mm $\phi \times 50H$) to a first coagulation solution of ethyl acetate and then passed through the second coagulation solution of methyl alcohol. The strand was introduced to a water bath and drawn to 1.34 times and winded. The obtained filament had 3.0 d and 1.1 g/d.

The obtained fiber was rinsed in a stream and immersed in ethyl alcohol. The filament was cut to about 5 mm and dispersed in water and a chitin fabric (Comparative Example 7) was formed according to the method of JIS P8209.

The nonwoven fabrics of Example 7 and Comparative Example 7 were cut to 10 cm in width and 10 cm in length and attached to a skin removed portion which was removed at a depth of 15/1000 inch in a back portion of rabbit by a dermatome. The wound portion was observed with time. The fabric of Comparative Example 7 was poor fitness and a dissolution was observed the next day, while the fabric of Example 7 was attached to an wound portion in good condition and no dissolutions were observed in one week, which indicates that the fabric is a good dressing.

COMPARATIVE EXAMPLE 8

0.5 g of the chitin fiber having 0.81 d and 3.4 g/d, obtained in Example 7 and 0.05 g of polyvinyl alcohol powder having a particle size of 20 mesh, a degree of polymerization of 1,700 and a degree of hydrolysis of 99.7% (available from Unitika Kasei Co. Ltd. as Unitika UF-170GM) were dispersed to one liter of water and a nonwoven fabric was formed as generally described in Example 1.

The obtained fabric was attached to a skin removed portion on the back of a rabbit having the depth of 15/1,000. It showed poor fitness and was broken after one day. It has been found that the PVA binder was not good for a binder.

COMPARATIVE EXAMPLE 9

The chitin fiber having 0.81 d and 3.4 g/d obtained in Example 7 was treated with a 0.1N hydrochloric acid for one hour to change the strength to 1.3 g/d. The filament was cut to 5 mm and a nonwoven fabric was formed as generally described in Example 1.

The obtained fabric was attached to a skin removed portion on the back of the rabbit having the depth of 15/1,000. It showed a partial decomposition by exudate after two days, which indicated that the fabric was not good for a wound dressing.

Since the wound dressing has good fitness to a wound, a resistance property to exudate, and absorbs exudate in comparison with conventional collagen fabrics or freeze-dried pig-skins, the wound dressing of the present invention, when applied to a dressing for skin defect wounds such as burns, a donor site and a skin-grafted portion, heals the wounds rapidly in a good condition. Accordingly, the wound dressing is suitable as a dressing for deep wounds.

What is claimed is:

1. A wound dressing comprising a nonwoven fabric composed of
   (A) a chitin fiber having a thickness of less than one denier and a strength of not less than 2 g/d, and
   (b) a fibrous binder.

2. The dressing of claim 1 in which the chitin fiber has a thickness of more than 0.2 denier and less than 1 denier.

3. The dressing of claim 1 in which the fibrous binder is formed from polyvinyl alcohol, carboxymethyl cellulose, gelatin, starch, acrylic acid ester, vinyl acetate, ethylene, vinyl acetate copolymer, vinyl chloride, natural rubber or synthetic rubber.

4. The dressing of claim 1 in which the weight ratio of the chitin fiber to the fibrous binder is within the range of from 80:20 to 95:5.

* * * * *